United States Patent [19]
Nakazato et al.

[11] Patent Number: 6,166,033
[45] Date of Patent: Dec. 26, 2000

[54] 2-CARBONYLTHIAZOLE DERIVATIVES AND USE OF THE SAME

[75] Inventors: Atsuro Nakazato; Toshihito Kumagai; Shigeyuki Chaki; Kazuyuki Tomisawa, all of Tokyo; Masashi Nagamine, Osaka; Makoto Gotoh, Osaka; Masanori Yoshida, Osaka, all of Japan

[73] Assignees: Taisho Pharmaceutical Co., Ltd.; Nihon Nohyaku Co., Ltd., both of Japan

[21] Appl. No.: 09/269,021

[22] PCT Filed: Sep. 19, 1997

[86] PCT No.: PCT/JP97/03342

§ 371 Date: Nov. 5, 1999

§ 102(e) Date: Nov. 5, 1999

[87] PCT Pub. No.: WO98/12195

PCT Pub. Date: Mar. 26, 1998

[30] Foreign Application Priority Data

Sep. 20, 1996 [JP] Japan .................................. 8-249415

[51] Int. Cl.[7] .................. A61K 31/4535; A61K 31/496; C07D 413/06; C07D 211/70; C07D 401/14
[52] U.S. Cl. .................. 514/316; 514/236.8; 514/253.1; 514/326; 544/129; 544/360; 546/186; 546/187; 546/209
[58] Field of Search ................................ 514/236.8, 252, 514/316, 326, 253.1; 544/129, 360; 546/186, 187, 209

[56] References Cited

U.S. PATENT DOCUMENTS 4,123,529  10/1978  Verge et al. ............................ 424/250
5,071,864  12/1991  Rendenbach-Mueller et al. .... 514/370
5,401,762   3/1995  Rendenbach-Mueller et al. .... 514/369

FOREIGN PATENT DOCUMENTS

409048A2   1/1991   European Pat. Off. .
9222539   12/1992   WIPO .
9629330    9/1996   WIPO .

*Primary Examiner*—Mukund J. Shah
*Assistant Examiner*—Ben Schroeder
*Attorney, Agent, or Firm*—Lorusso & Loud

[57] ABSTRACT

This invention provides a 2-carbonylthiazole derivative represented by formula (I):

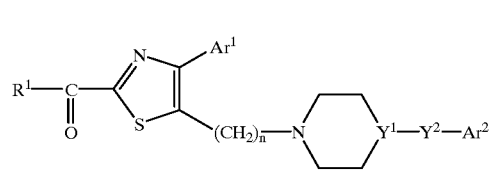

wherein each of $Ar^1$ and $Ar^2$ represents a phenyl group or a substituted phenyl group; $R^1$ represents an alkoxy group having 1 to 5 carbon atoms, a hydroxyl group or an amino group; $Y^1$—$Y^2$ represents CH—CO or C=$CR^2$, wherein $R^2$ represents a hydrogen atom or an alkyl group having 1 to 5 carbon atoms; and n is an integer of from 1 to 4, or a pharmaceutically acceptable salt thereof. The disclosed compounds are useful as drugs for preventing and treating dopamine D receptor-related morbid states such as schizophrenia and problematic behavior caused by cerebrovascular accidents and senile dementia and do not induce extrapyramidal disorders as side effects.

8 Claims, No Drawings

2-CARBONYLTHIAZOLE DERIVATIVES AND USE OF THE SAME

TECHNICAL FIELD

This invention relates to a 2-carbonylthiazole derivative having antipsychotic action.

BACKGROUND ART

Antipsychotic drugs are used for the treatment of not only schizophrenia but also problematic behavior (such as aggressive behavior, mental excitation, poriomania and delirium) caused by cerebrovascular accidents and senile dementia. However, the conventional antipsychotic drugs, dopamine $D_2$ receptor antagonists, have a serious problem in that they cause strong extrapyramidal disorders as their side effects.

On the other hand, the structure and properties of recently discovered dopamine $D_4$ receptor are close to those of dopamine $D_2$ receptor, and a great difference between them is their intracerebral distribution. Regarding the intracerebral distribution of dopamine $D_4$ receptor, it is distributed in a high concentration in the cerebral cortex frontal lobe which is related to the onset of schizophrenia, but in a small amount in the striate body which is concerned in the expression of extrapyramidal disorders. In consequence, dopamine $D_4$ receptor antagonists have a great possibility to be used as novel schizophrenia treating drugs which do not accompany extrapyramidal disorders as the side effects that are common in dopamine $D_2$ receptor antagonists (*Nature*, 350, 610–614 (1991); *Nature*, 358, 109 (1992); *Nature*, 365, 393 (1993); *Nature*, 365, 441–445 (1993)).

Clozapine is one of such compounds. It has been reported that affinity of clozapine for dopamine $D_4$ receptor is higher than its affinity for dopamine $D_2$ receptor (*Nature*, 350, 610–614 (1991)). It has been reported also that, unlike the case of dopamine $D_2$ receptor antagonists, clozapine is effective in drug-resistant schizophrenia and negative symptoms and causes less extrapyramidal disorders, according to its clinical investigation (*Arch. Gen. Psych.*, 45, 789–796 (1988)). However, clozapine has a serious disadvantage in that it generates a hemotoxin as agranulocytosis which resulted in certain mortal cases (Summary and Clinical Data, Sandoz, Canada Inc. (1990)).

In consequence, such a dopamine $D_4$ receptor antagonist having no side effects is highly useful as a drug for the treatment of diseases such as schizophrenia, having an extremely low possibility of causing extrapyramidal disorders.

DISCLOSURE OF THE INVENTION

An object of the present invention is to provide a dopamine $D_4$ receptor antagonistic compound which shows antipsychotic action without generating extrapyramidal disorders.

The inventors of the present invention have conducted intensive studies on 2-carbonylthiazole derivatives and found as a result of the efforts a novel 2-carbonylthiazole derivative which shows high affinity for dopamine $D_4$ receptor, thereby accomplishing the present invention.

The following describes the present invention.

The present invention is a 2-carbonylthiazole derivative represented by formula (I):

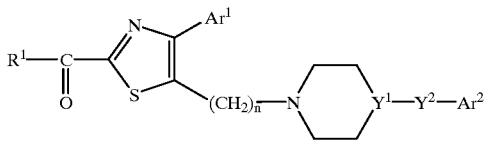

[wherein each of $Ar^1$ and $Ar^2$ represents a phenyl group, a phenyl group having one or two substituents selected from "a halogen atom, an alkyl group having 1 to 5 carbon atoms, a trifluoromethyl group, an alkoxy group having 1 to 5 carbon atoms and a hydroxyl group" or a thienyl group; $R^1$ represents an alkoxy group having 1 to 5 carbon atoms, a hydroxyl group or an amino group represented by formula $N(R^3)R^4$ (wherein each of $R^3$ and $R^4$ represents a hydrogen atom or an alkyl group having 1 to 5 carbon atoms, or $R^3$ and $R^4$, together with the nitrogen atom to which they are bound, form a pyrrolidino, piperidino, morpholino or piperazino group, or a pyrrolidino, piperidino, morpholino or piperazino group having one to four substituents selected from "an alkyl group having 1 to 5 carbon atoms, an alkoxy group having 1 to 5 carbon atoms and a hydroxyl group"); $Y^1$—$Y^2$ represents CH—CO or C=C($R^2$) (wherein $R^2$ represents a hydrogen atom or an alkyl group having 1 to 5 carbon atoms); and n is an integer of from 1 to 4] or a pharmaceutically acceptable salt thereof.

In the definition of the present invention, the term "halogen atom" means a fluorine atom, a chlorine atom, a bromine atom or an iodine atom. The term "alkyl group having 1 to 5 carbon atoms" means a straight- or branched-chain alkyl group, and the term "alkoxy group having 1 to 5 carbon atoms" means a straight- or branched-chain alkoxy group. Thus, examples of the phenyl group having substituent(s) represented by $Ar^1$ and $Ar^2$ include 2-fluorophenyl, 3-fluorophenyl, 4-fluorophenyl, 4-chlorophenyl, 4-bromophenyl, 3,4-dichlorophenyl, 4-methylphenyl, 3-trifluoromethylphenyl, 4-methoxyphenyl, 3,4-dimethoxyphenyl, 4-hydroxyphenyl and the like groups. Also, examples of the amino group represented by formula $N(R^3)R^4$ include amino, methylamino, dimethylamino, ethylamino, propylamino, isopropylamino, dipropylamino, pyrrolidino, 3-hydroxypyrrolidino, piperidino, 3-methoxypiperidino, morpholino, piperazino, N-methylpiperazino and the like groups.

The alkyl group having 1 to 5 carbon atoms represented by $R^2$ is a straight chain alkyl group, a branched-chain alkyl group or a cyclic alkyl group, and its examples include methyl, ethyl, propyl, isopropyl, butyl, isobutyl, cyclopropylmethyl, cyclobutyl and the like groups.

In addition, examples of the pharmaceutically acceptable salt of the present invention include salts with mineral acids such as sulfuric acid, hydrochloric acid and phosphoric acid, salts with organic carboxylic acids such as acetic acid, oxalic acid, lactic acid, tartaric acid, citric acid, fumaric acid, maleic acid and trifluoroacetic acid and salts with organic sulfonic acids such as methanesulfonic acid and benzenesulfonic acid. Also, monovalent or divalent metal salts can be exemplified as salts which are formed when $R^1$ is a hydroxyl group, and examples of the metal in this case include sodium, potassium, lithium and calcium.

A preferred compound of the present invention is a 2-carbonylthiazole derivative represented by formula (II):

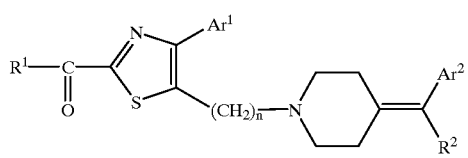

(wherein $Ar^1$, $Ar^2$, $R^1$, $R^2$ and n are as defined in the foregoing) or a pharmaceutically acceptable salt thereof.

More preferred is a 2-carbonylthiazole derivative represented by formula (III):

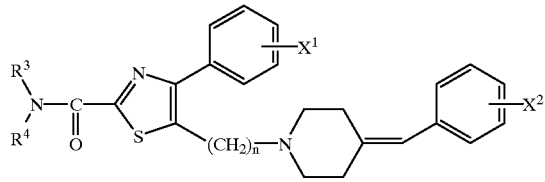

(wherein $R^3$ and $R^4$ and n are as defined in the foregoing, and each of $X^1$ and $X^2$ is a hydrogen atom, a halogen atom or an alkyl group having 1 to 5 carbon atoms) or a pharmaceutically acceptable salt thereof, in which particularly preferred is a compound or a pharmaceutically acceptable salt thereof wherein $R^3$ and $R^4$ are both hydrogen atoms, and $X^1$ and $X^2$ are both 4-position substituted fluorine atoms, $X^1$ is a hydrogen atom and $X^2$ is a 4-position substituted fluorine atom or $X^1$ is a 4-position substituted fluorine atom and $X^2$ is a 3-position substituted fluorine atom.

The compound of formula (I) can be produced by the following methods (in the following reaction formulae, $Ar^1$, $Ar^2$, $R^1$, $R^2$, $R^3$, $R^4$, $Y^1$, $Y^2$, $X^1$, $X^2$ and n are as defined in the foregoing, $R^5$ is an alkyl group having 1 to 5 carbon atoms represented by $R^1$, $R^6$ is $R^1$ excluding a hydrogen atom, $R^7$ is an alkyl group having 1 to 5 carbon atoms or two $R^7$ groups are bound to each other by single bond to form an alkylene group, $R^8$ is a protecting group of the nitrogen atom, which includes alkoxycarbonyl groups such as t-butoxycarbonyl and ethoxycarbonyl, acyl groups such as acetyl and benzoyl, sulfonyl groups such as tosyl, an alkyl group having 1 to 5 carbon atoms or benzyl group, $R^9$ is an alkyl group having 1 to 5 carbon atoms, $X^3$ is a chlorine atom, a bromine atom or an iodine atom, and M is an alkali or alkaline earth metal atom such as sodium, potassium, lithium or ½ calcium or a hydrogen atom).

(Reaction formula 1)

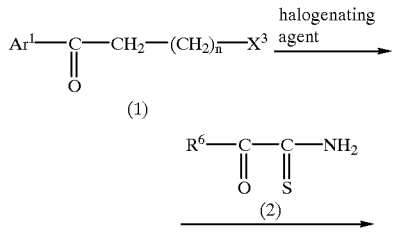

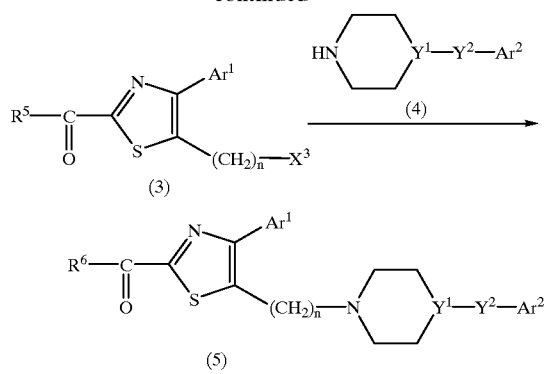

A compound of the present invention represented by the formula (5) can be obtained by carrying out halogenation of a ketone compound (1) with a halogenating agent in an inert solvent, allowing the halogenated compound to react with a thioamide derivative (2) in an inert solvent in the presence or absence of a dehydrating agent or a base, thereby converting it into a thiazole derivative (3), and then allowing the resulting derivative to react with a piperidine derivative (4) in an inert solvent in the presence or absence of a base.

Examples of the inert solvent to be used in this case include organic carboxylic acids such as acetic acid, organic halogen compounds such as chloroform and carbon tetrachloride, alcohols such as ethanol and isopropanol, ethers such as diethyl ether and tetrahydrofuran, hydrocarbons such as toluene, N,N-dimethylformamide, acetonitrile and water, or a mixed solvent thereof. Examples of the dehydrating agent include molecular sieves such as Molecular Sieves 3A and Molecular Sieves 4A, inorganic salts such as anhydrous sodium sulfate, anhydrous magnesium sulfate and anhydrous calcium chloride, and phosphorus pentaoxide. Examples of the base include inorganic bases such as potassium carbonate, sodium carbonate, potassium bicarbonate and sodium bicarbonate, alcholates such as sodium methoxide and potassium t-butoxide, alkali metal amides such as sodium amide, organic bases such as triethylamine, N,N-diisopropylethylamine, N-methylmorpholine and pyridine, and organic carboxylic acid salts such as sodium acetate. Examples of the halogenating agent include chlorine, bromine, iodine and sulfuryl chloride.

(Reaction formula 2)

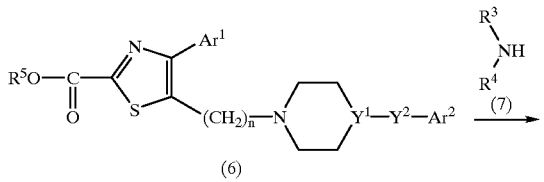

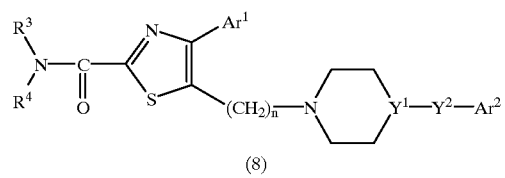

The 2-alkoxycarbonyl derivative (6) can be converted into a compound of the present invention represented by the formula (8) by treating with an amine (7) in an inert solvent in the presence or absence of an activating agent.

Examples of the inert solvent include organic halogen compounds such as chloroform and carbon tetrachloride, alcohols such as ethanol and isopropanol, ethers such as diethyl ether and tetrahydrofuran, hydrocarbons such as toluene, N,N-dimethylformamide, acetonitrile, and water, or a mixed solvent thereof. The activating agent is a substance which accelerates amidation of the carboxylic acid ester, such as sodium cyanide.

(Reaction formula 3)

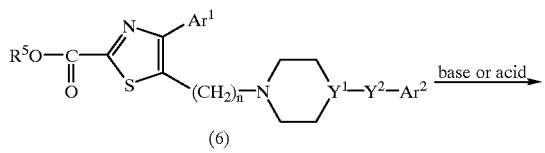

(6)

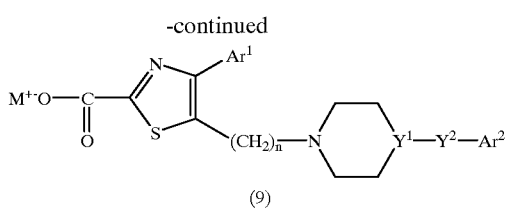

(9)

The 2-alkoxycarbonyl derivative (6) can be converted into a compound of the present invention represented by the formula (9) by hydrolyzing the carboxylic acid ester moiety in an inert solvent in the presence a base or acid.

Examples of the inert solvent include ethers such as diethyl ether, tetrahydrofuran and dioxane, alcohols such as methanol and ethanol, ketones such as acetone, organic carboxylic acids such as acetic acid, N,N-dimethylformamide, and water. Examples of the base include inorganic bases such as sodium hydroxide, potassium hydroxide, lithium hydroxide, barium hydroxide, calcium hydroxide and sodium carbonate, and examples of the acid include inorganic acids such as hydrochloric acid, hydrobromic acid and sulfuric acid and organic acids such as trifluoroacetic acid, formic acid, tosylic acid and methanesulfonic acid.

(Reaction formula 4)

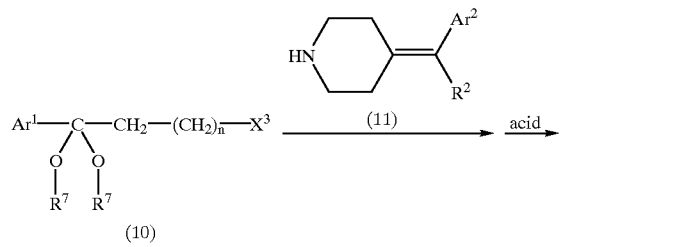

(10)

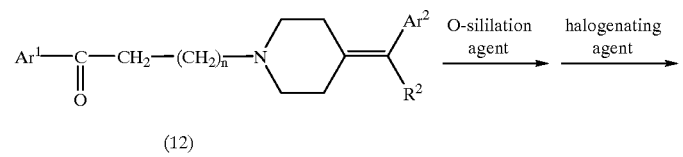

(12)

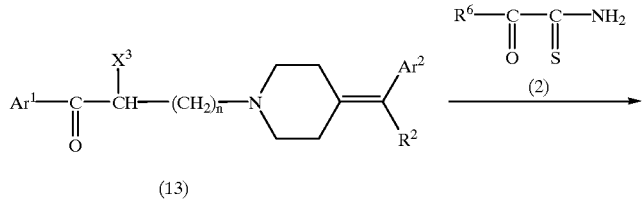

(13)

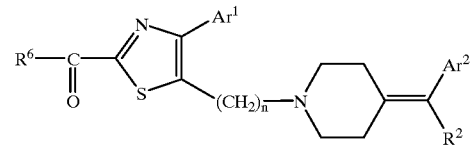

(14)

A ketone derivative (12) is obtained by allowing a ketal derivative (10) to react with a benzylidenepiperidine derivative (11) in the presence or absence of a base in an inert solvent or without solvent and then treating the resulting product with an acid in an inert solvent.

Examples of the base include organic amines such as triethylamine, N,N-diisopropylethylamine, N-methylmorpholine and pyridine and inorganic bases such as potassium carbonate, sodium carbonate, potassium bicarbonate, sodium bicarbonate, potassium hydroxide, sodium hydroxide and sodium hydride. Examples of the inert solvent to be used in the first step include ethers such as diethyl ether, tetrahydrofuran and dioxane, hydrocarbons such as benzene and toluene, alcohols such as ethanol, N,N-dimethylformamide, acetonitrile, and water, or a mixed solvent thereof. Examples of the inert solvent to be used in the second step include ethers such as diethyl ether, tetrahydrofuran and dioxane, alcohols such as ethanol, organic carboxylic acid esters such as ethyl acetate, ketones such as acetone, alkyl halides such as dichloromethane and chloroform, organic carboxylic acids such as acetic acid, N,N-dimethylformamide, and water, or a mixed solvent thereof. Examples of the acid include inorganic acids such as hydrochloric acid, hydrobromic acid and sulfuric acid and organic acids such as trifluoroacetic acid, formic acid, tosylic acid and methanesulfonic acid, or salts of these organic acids with pyridine.

The ketone derivative (12) is converted into a haloketone derivative (13) by allowing to react with an O-sililation agent in an inert solvent in the presence of a base, thereby converting it into a vinyl silyl ether, and then allowing the ether to react with a halogenating agent in an inert solvent. The haloketone derivative (13) is allowed to react with the thioamide derivative (2) in the same manner as shown in the (Reaction formula 1), thereby obtaining a compound of the present invention represented by the formula (14).

Examples of the inert solvent to be used in the O-sililation include ethers such as diethyl ether, tetrahydrofuran and dioxane, hydrocarbons such as benzene and toluene, N,N-dimethylformamide, and acetonitrile. Examples of the base include alkali metal amides such as lithium diisopropylamide, sodium bis(trimethylsilyl)amide and sodium amide, alkali metal hydrides such as sodium hydride and potassium hydride and organic amines such as triethylamine and N,N-diisopropylethylamine, which may be used jointly with sodium iodide or potassium iodide as occasion demands. The O-sililation agent means various sililation agents, including a halotrialkylsilane such as chlorotrimethylsilane. Examples of the inert solvent to be used in the halogenation include organic halogen compounds such as chloroform and carbon tetrachloride, alcohols such as ethanol and isopropanol, ethers such as diethyl ether and tetrahydrofuran, hydrocarbons such as benzene and toluene, N,N-dimethylformamide, acetonitrile, and water, or a mixed solvent thereof. Examples of the halogenating agent include halogens such as chlorine, bromine and iodine, N-haloimides such as N-chlorosuccinimide and N-bromosuccinimide, and metal halides such as cupric chloride, cupric bromide and ferric chloride.

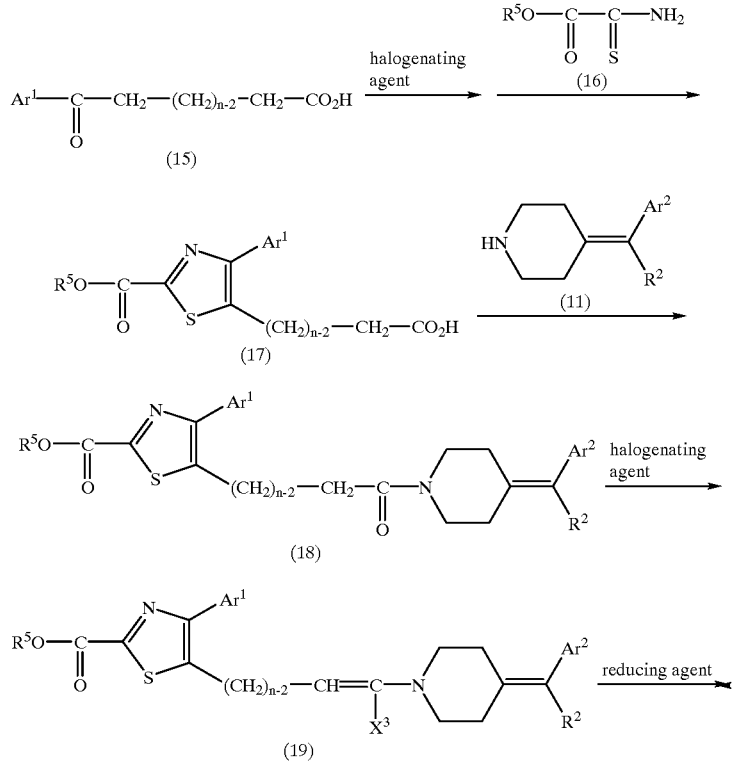

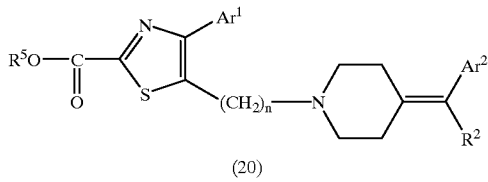

(20)

The ketocarboxylic acid (15) can be converted into a thiazolecarboxylic acid derivative (17) by halogenating in the same manner as shown in (Reaction formula 1) and then allowing to react with a thioamide derivative (16).

The thiazolecarboxylic acid derivative (17) can be converted into an amide derivative represented by the formula (18) via an acid halide or mixed acid anhydride or by allowing it to react with a benzylidenepiperidine derivative (11) together with a condensing agent.

A compound of the present invention represented by the formula (20) can be obtained by allowing the amide compound (18) to react with a halogenating agent, for example, in accordance with the method described in *Journal of Organic Chemistry*, 42, 2082 (1977) and then to react with a reducing agent.

tetrahydrofuran, a hydrocarbon such as toluene or benzene, a halogen solvent such as chloroform or dichloromethane, acetonitrile, and N,N-dimethylformamide. The condensing agent means a usually used amidation reagent which includes diphenylphosphoryl azide, diethyl cyanophosphate, carbonyldiimidazole, and carbodiimides such as N,N'-dicyclocarbodiimide and N-ethyl-N'-dimethylaminopropylcarbodiimide hydrochloride, and is used together, as occasion demands, with N-hydroxysuccinimide, 1-hydroxybenzotriazole or 3-hydroxy-4-oxo-3,4-dihydro-1,2,3-benzotriazine, in an inert solvent which includes an ether such as 1,2-dimethoxyethane or tetrahydrofuran, a hydrocarbon such as toluene or benzene, a halogen solvent such as chloroform or dichloromethane, acetonitrile, and N,N-dimethylformamide.

(Reaction formula 6)

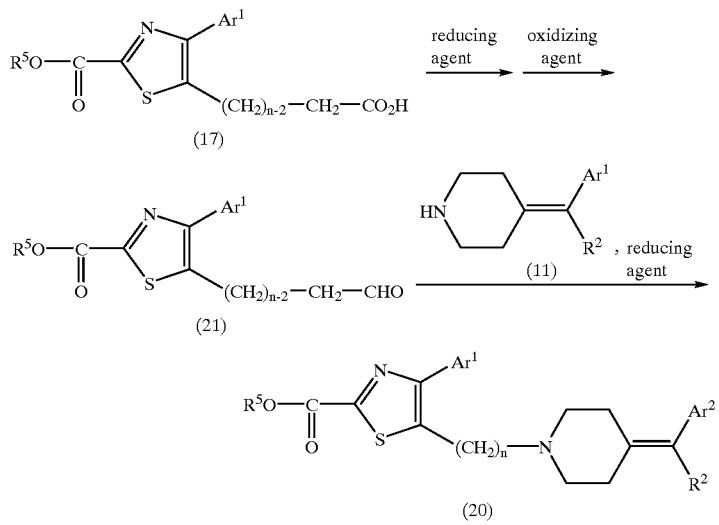

In this case, the acid halide means an acid chloride or an acid bromide which can be obtained for example by allowing a halogenating agent such as thionyl chloride, oxalyl chloride or carbon tetrachloride-triphenylphosphine to undergo the reaction in an inert solvent including an ether such as tetrahydrofuran, a hydrocarbon such as toluene or benzene, a halogen solvent such as chloroform or dichloromethane, acetonitrile, and N,N-dimethylformamide. The mixed acid anhydride means anhydride of a carboxylic acid and carbonic acid, and can be obtained, for example, by allowing a halocarbonic acid ester such as ethyl chlorocarbonate or isobutyl chlorocarbonate to undergo the reaction in the presence of an organic base such as triethylamine, diisopropylethylamine, N-methylmorpholine or pyridine, or an inorganic base such as sodium hydride or sodium carbonate, in an inert solvent including an ether such as The compound of the present invention represented by the formula (20) can be obtained by converting the thiazolecarboxylic acid derivative (17) into a thiazolealdehyde derivative (21) through reduction of its carboxylic acid moiety using a reducing agent and subsequent oxidation of the alcohol using an oxidizing agent, and then allowing the aldehyde derivative to react with a benzylidenepiperidine derivative (11) in the presence of a reducing agent.

In this case, the reducing agent of carboxylic acid means a selective reducing agent of carboxylic acid, such as diborane or borane-tetrahydrofuran complex, and is used in an inert solvent which includes an ether such as 1,2-dimethoxyethane or tetrahydrofuran and a hydrocarbon such as toluene or benzene. Examples of the oxidizing agent of alcohol include a Swern's oxidation system which uses oxalyl Chloride-dimethyl sulfoxide, a chrome based oxidizing agent and a metallic oxidizing agent such as manganese dioxide, which are used in an inert solvent including ethers such as 1,2-dimethoxyethane and tetrahydrofuran, hydrocarbons such as toluene and benzene, halogen solvents such as chloroform and dichloromethane, acetonitrile, N,N-dimethylformamide, and acetone. Examples of the reducing agent to be used in the final step include diborane, borane-tetrahydrofuran complex, sodium borohydride and sodium cyanoborohydride, and the reaction is carried out in an inert solvent selected from alcohols such as ethanol and isopropanol, ethers such as diethyl ether and tetrahydrofuran, and hydrocarbons such as benzene and toluene, if necessary by adding an acid such as hydrochloric acid, hydrogen chloride or acetic acid.

(Reaction formula 7)

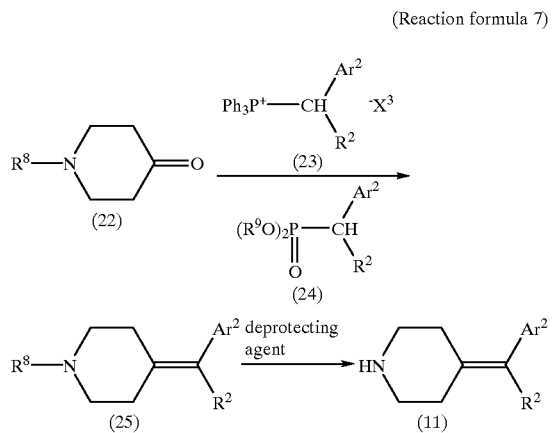

A 4-benzylidenepiperidine derivative represented by the formula (11) can be obtained by condensing a piperidone derivative (22) with a triphenylarylmethyl phosphonium salt (23) or a dialkylarylmethyl phosphonate (24) in an inert solvent in the presence of a base and then eliminating the protecting group using a deprotecting agent.

Examples of the base include sodium hydride, potassium hydride, sodium methoxide, potassium t-butoxide, n-butyl lithium, lithium diisopropylamide, lithium bis(trimethylsilyl)amide and sodium amide, which, as occasion demands, may be used jointly with a catalyst such as 15-crown-5 ether or 18-crown-6 ether, or tetramethylethylenediamine or hexamethylphosphoramide. Examples of the inert solvent include ethers such as diethyl ether, tetrahydrofuran and dioxane, hydrocarbons such as benzene and toluene, alcohols such as ethanol, N,N-dimethylformamide, dimethyl sulfoxide, and water. Examples of the reaction solvent at the time of deprotection include ethers such as diethyl ether, tetrahydrofuran and dioxane, hydrocarbons such as benzene and toluene, alcohols such as ethanol, organic carboxylic acid esters such as ethyl acetate, ketones such as acetone, alkyl halides such as dichloromethane and chloroform, organic carboxylic acids such as acetic acid, N,N-dimethylformamide, and water. When $R^4$ is an alkoxycarbonyl group, an acyl group or a sulfonyl group, examples of the deprotecting agent include inorganic acids such as hydrochloric acid, hydrobromic acid and sulfuric acid, organic acids such as trifluoroacetic acid, formic acid and methanesulfonic acid and dioxane solution or ethyl acetate solution of hydrogen chloride, and inorganic bases such as sodium hydroxide, potassium hydroxide and barium hydroxide. When $R^4$ is an alkyl group having 1 to 5 carbon atoms or a benzyl group, such a group is firstly converted into an alkoxycarbonyl group by allowing to react with an alkyl haloformate such as ethyl chloroformate in the presence or absence of a base and then subjected to deprotection in the same manner. Alternatively, when $R^4$ is a benzyl group, deprotection can be effected by Birch's reduction.

The compound of the present invention has superior affinity for dopamine $D_4$ receptor but low affinity for dopamine $D_2$ receptor, thus showing excellent selectivity. In consequence, the compound of the present invention is useful as a drug for the prevention and treatment of diseases such as schizophrenia and problematic behavior caused by cerebrovascular accidents and senile dementia and also as said drug which does not induce extrapyramidal disorders as side effects.

For use in such a purpose, the compound of the present invention can be made into tablets, pills, capsules, granules, powders, solutions, emulsions, suspensions or injections by the ordinary preparation techniques after mixing it with usually used additives such as fillers, binders, disintegrating agents, pH adjusting agents and solubilizing agents.

The compound of the present invention can be administered orally or parenterally to patients in a dose of from 0.1 to 500 mg/day per adult, once a day or by dividing the daily dose into several doses per day. Such a range of dose can be changed optionally depending on the type of diseases and age, body weight and symptoms of each patient.

BEST MODE OF CARRYING OUT THE INVENTION

The following illustratively describes the present invention with reference to inventive and test examples.

EXAMPLE 1

Synthesis of 2-ethoxycarbonyl-5-(2-chloroethyl)-4-(4-fluorophenyl)thiazole 50.00 g of 4-chloro-4'-fluorobutyrophenone was dissolved in 250 ml of carbon tetrachloride to which was subsequently added dropwise 41.30 g of bromine over 30 minutes. The reaction mixture was stirred at room temperature for 1 hour and then concentrated under reduced pressure.

The residue and 33.20 g of ethyl thiooxamate were stirred in 250 ml of ethanol under reflux for 15 hours. The reaction mixture was concentrated under reduced pressure, the residue, after addition of ethyl acetate, was washed with saturated aqueous sodium bicarbonate and saturated brine, and dried over anhydrous sodium sulfate, the drying agent was removed by filtration and then the resulting filtrate was concentrated under reduced pressure. The resulting residue was purified by a flash column chromatography (silica gel: Wako Gel C200 (manufactured by Wako Pure Chemical Industries), eluant: hexane-ethyl acetate=10:1–9:1) and then recrystallized from diisopropyl ether to obtain 29.14 g of 2-ethoxycarbonyl-5-(2-chloroethyl)-4-(4-fluorophenyl) thiazole.

m.p. 81.5–82.5° C.

The following compounds were obtained in the same manner.

2-Ethoxycarbonyl-5-(2-chloroethyl)-4-phenylthiazole
NMR (CDCl$_3$)δ(ppm); 1.44 (3 H, t, J=7.1), 3.41–3.77 (4 H, m), 4.49 (2 H, q, J=7.1), 7.27–7.61 (5 H, m)
MS m/e; 298 (M$^+$+1), 296 (M$^+$+1), 59 (100%)
2-Ethoxycarbonyl-5-(2-chloroethyl)-4-(4-methylphenyl) thiazole
m.p. 79.0–80.0° C. (recrystallized from diisopropyl ether)
2-Carbamoyl-5-(2-chloroethyl)-4-(4-fluorophenyl)thiazole
m.p. 136.0–138.0° C. (recrystallized from ether-hexane)
2-Methoxycarbonyl-5-(2-chloroethyl)-4-phenylthiazole
m.p. 80.0–82.0° C. (stand after flash column chromatography) 2-Ethoxycarbonyl-5-(2-bromoethyl)-4-phenylthiazole NMR (CDCl$_3$)δ(ppm); 1.44 (3 H, t, J=7.1), 3.54–3.57 (4 H, m), 4.49 (2 H, q, J=7.1), 7.27–7.61 (5 H, m)

MS m/e; 342 (M$^+$+1), 340 (M$^+$+1), 59 (100%)

2-Ethoxycarbonyl-5-(2-bromoethyl)-4-(4-methylphenyl)thiazole

NMR (CDCl$_3$)δ(ppm); 1.44 (3 H, t, J=7.1), 2.40 (3 H, s), 3.53–3.56 (4 H, m), 4.49 (2 H, q, J=7.1), 7.24–7.28 (2 H, m), 7.45–7.50 (2 H, m)

MS m/e; 356 (M$^+$+1), 354 (M$^+$+1, 100%)

2-Ethoxycarbonyl-5-(2-bromoethyl)-4-(4-fluorophenyl)thiazole

NMR (CDCl$_3$)δ(ppm); 1.44 (3 H, t, J=7.1), 3.46–3.60 (4 H, m), 4.49 (2 H, q, J=7.1), 7.11–7.20 (2 H, m), 7.54–7.61 (2 H, m)

MS m/e; 360 (M$^+$+1), 358 (M$^+$+1, 100%)

EXAMPLE 2

Synthesis of 2-ethoxycarbonyl-4-(4-fluorophenyl)-5-[2-[4-(3-fluorobenzylidene)piperidin-1-yl]ethyl]thiazole hydrochloride 1.50 g of 2-ethoxycarbonyl-4-(4-fluorophenyl)-5-(2-chloroethyl)thiazole, 1.10 g of 4-(3-fluorobenzylidene)piperidine hydrochloride and 2.50 g of N,N-diisopropylethylamine were stirred in 3 ml of ethanol at 80° C. for 40 hours. The reaction solution was concentrated under reduced pressure, and the residue was treated with ethyl acetate and saturated aqueous sodium bicarbonate to effect separation of layers. The organic layer was washed with saturated brine and dried over anhydrous sodium sulfate, and then the drying agent was removed by filtration. The resulting filtrate was concentrated under reduced pressure, and the residue was purified by a flash column chromatography (Wako Gel C200 (manufactured by Wako Pure Chemical Industries), eluant: hexane-ethyl acetate–5.1) and then Chromatolex NH NHDM1020 (manufactured by Fuji Division Chemical), eluant: hexane-ethyl acetate=10.1). This product was treated with 4 N hydrogen chloride/1.4-dioxane solution and then recrystallized from ethanol to obtain 1.14 g of 2-ethoxycarbonyl-4-(4-fluorophenyl)-5-[2-[4-(3-fluorobenzylidene)piperidin-1-yl]ethyl]thiazole hydrochloride m.p. 206.5–207.5° C.

Structures and physical property data of this compound and other compounds obtained in the same manner are shown in Table 1.

EXAMPLE 3

Synthesis of 2-carbamoyl-4-(4-fluorophenyl)-5-[2-[4-(3-fluorobenzylidene)piperidin-1-yl]ethyl]thiazole 315 mg of 2-ethoxycarbonyl-4-(4-fluorophenyl)-5-[2-[4-(3-fluorobenzylidene)piperidin-1-yl]ethyl]thiazole and 0.05 ml of 28% aqueous ammonia were stirred in 1.5 ml of ethanol for 3 days. To the mixture was added 0.50 ml of 28% aqueous ammonia to carry out additional 3 days of reaction. The reaction solution was concentrated under reduced pressure, and the resulting residue was purified by a flash column chromatography (Wako Gel C200 (manufactured by Wako Pure Chemical Industries), eluant: hexane-ethyl acetate=3:1–1:1) and recrystallized from ethanol to obtain 201 mg of 2-carbamoyl-4-(4-fluorophenyl)-5-[2-[4-(3-fluorobenzylidene)piperidin-1-yl]ethyl]thiazole.

m.p. 171.5–172.5° C.

Structures and physical property data of this compound and other compounds obtained in the same manner are shown in Table 1.

EXAMPLE 4

Synthesis of 2-carboxylic acid-4-(4-fluorophenyl)-5-[2-[4-(3-fluorobenzylidene)piperidin-1-yl]ethyl]thiazole potassium salt To 277 mg of 2-ethoxycarbonyl-4-(4-fluorophenyl)-5-[2-[4-(3-fluorobenzylidene)piperidin-1-yl]ethyl]thiazole was added 0.33 ml of 2 N potassium hydroxide aqueous solution and the mixture was stirred overnight. The reaction solution was concentrated under reduced pressure, and the resulting residue was purified by a column chromatography (DIAION HP20 (manufactured by Mitsubishi Kagaku), water→50% ethanol→ethanol) to obtain 209 mg of 2-carboxylic acid-4-(4-fluorophenyl)-5-[2-[4-(3-fluorobenzylidene)piperidin-1-yl]ethyl]thiazole potassium salt.

NMR (CDCl$_3$)δ(ppm); 2.30–2.63 (10 H, m), 3.00–3.10 (2 H, m), 6.30 (1 H, s), 6.99–7.07 (3 H, m), 7.23–7.43 (3 H, m), 7.62–7.69 (2 H, m)

MS m/e; 517 (M$^+$+K), 479 (M$^+$+1), 204 (100%)

Structures and physical property data of this compound and other compounds obtained in the same manner are shown in Table 1.

EXAMPLE 5

Synthesis of 2-carbamoyl-4-phenyl-5-[2-[4-(4-fluorobenzylidene)piperidin-1-yl]ethyl]thiazole (1) A mixture of 6.80 g of 2-phenyl-2-(3-chloropropryl)-1,3-dioxolan, 6.83 g of 4-(4-fluorobenzylidene)piperidine hydrochloride and 16 ml of N,N-diisopropylethylamine in 16 ml of methanol was stirred at 80° C. for 50 hours. The reaction solution was concentrated under reduced pressure, saturated aqueous sodium bicarbonate and chloroform were added to the residue, and then the organic layer was separated. The organic layer was washed with water and dried over anhydrous magnesium sulfate, the drying agent was removed by filtration, and then the resulting filtrate was concentrated under reduced pressure.

To the residue was added 30 ml of 2 N hydrochloric acid and 30 ml of tetrahydrofuran, and the mixture was stirred at room temperature for 16 hours. The reaction solution was concentrated under reduced pressure, 2 N sodium hydroxide aqueous solution and ethyl acetate were added to the residue, and then the organic layer was separated. The aqueous layer was further extracted with ethyl acetate, the organic layers were combined, washed with saturated brine and dried over anhydrous magnesium sulfate, and then the drying agent was removed by filtration. The resulting filtrate was concentrated under reduced pressure, and the residue was purified by a flash column chromatography (Merck Silica Gel 230–400 mesh, eluant: hexane-ethyl acetate=1:1) and crystallized from hexane to obtain 7.36 g of 1-(4-phenyl-4-oxobutyl)-4-(4-fluorobenzylidene)piperidine.

(2) While cooling at −50° C., to a solution of lithium diisopropylamide prepared from 2.1 ml of diisopropylamine and 10 ml of 1.63 M n-butyl lithium tetrahydrofuran (15 ml) was added dropwise a solution of 5.24 g of 1-(4-phenyl-4-oxobutyl)-4-4-fluorobenzylidene)piperidine in 20 ml of tetrahydrofuran. After completion of the dropwise addition, the mixture was stirred for 20 minutes and then thereto was added 3 ml of trimethylsilyl chloride. Thereafter, the reaction solution was gradually warmed up and stirred at room temperature for 16 hours. To the reaction mixture was added chloroform and saturated aqueous sodium bicarbonate while cooling in an ice bath, and then the organic layer was separated. The aqueous layer was further extracted with chloroform, and the organic layers were combined and washed with water. This was dried over anhydrous magnesium sulfate, the drying agent was removed by filtration, and then the resulting filtrate was concentrated under reduced pressure to obtain 6.21 g of 1-(4-phenyl-4-trimethylsilyloxy-3-buten-1-yl)-4-(4-fluorobenzylidene)piperidine).

(3) 6.21 g of 1-(4-phenyl-4-trimethylsilyloxy-3-buten-1-yl)-4-(4-fluorobenzylidene)piperidine was dissolved in 30 ml of tetrahydrofuran, and 2.83 g of N-bromosuccinimide was added in small portions to the thus prepared solution which was cooled at −50° C. The reaction mixture was further stirred at −50° C. for 1 hour and gradually warmed to −20° C., and then thereto was added saturated aqueous sodium bicarbonate and chloroform, subsequently separating the organic layer. The aqueous layer was further extracted with chloroform, and the organic layers were combined and washed with water. After drying over anhydrous magnesium sulfate, the drying agent was removed by filtration, and 8 ml of 4 N hydrogen chloride dioxane solution was added to the resulting filtrate which was cooled in an ice bath. The solvent was evaporated under reduced pressure, and the resulting residue was crystallixed from ether to obtain 6.00 g of 1-(3-bromo-4-phenyl-4-oxobutyl)-4-(4-fluorobenzylidene)piperidine hydrochloride.

5.90g of 1-(3-bromo-4-phenyl-4-oxobutyl)-4-(4-fluorobenzylidene)piperidine hydrochloride was mixed with 2.26 g of ethyl thiooxamate and 3.26 g of Molecular Sieves 4A in 25 ml of 1,2-dimethoxyethane, and the mixture was heated under reflux for 12 hours with stirring. After cooling to room temperature, the thus precipitated matter was collected by filtration and washed with ether. This was disolved in chloroform, and the insoluble matter was removed by filtration. To the resulting filtrate was added 3.6 ml of triethylamine and then added chloroform and saturated aqueous sodium bicarbonate, and then the organic layer was separated. The aqueous layer was further extracted with chloroform, and the organic layers were combined and washed with water. After drying over anhydrous magnesium sulfate, the drying agent was removed by filtration and the resulting filtrate was concentrated under reduced pressure.

The residue was dissolved in 25 ml of ethanol, 8 ml of 28% aqueous ammonia was added thereto and then the mixture was stirred at room temperature for 3 days. The reaction solution was concentrated under reduced pressure, chloroform and water were added to the residue and then the organic layer was separated. The aqueous layer was further extracted with chloroform, and the organic layers were combined and washed with water. After drying over anhydrous magnesium sulfate, the drying agent was removed by filtration, the resulting filtrate was concentrated under reduced pressure and then the resulting residue was crystallized from ether to obtain 2.34 g of 2-carbamoyl-4-phenyl-5-[2-[4-(4-fluorobenzylidene)piperidin-1-yl]ethyl]thiazole.

Structures and physical property data of this compound and other compounds obtained in the same manner are shown in Table 1.

EXAMPLE 6

Synthesis of 4-(4-fluorobenzylidene)piperidine hydrochloride

A solution of 59.78 g of N-t-butoxycarbonylpiperidone and 81.25 g of diethyl 4-fluorobenzylphosphonate in 150 ml of tetrahydrofuran was added dropwise to a suspension of 13.20 g of 60% sodium hydride (in oil) containing 1.65 g of 15-crown-5 ether in 650 ml of tetrahydrofuran which was cooled in an ice bath over 20 minutes. After 1 day of stirring at room temperature, saturated aqueous sodium bicarbonate was carefully added to the reaction mixture which was subsequently extracted with ethyl acetate. The extract was washed with saturated aqueous sodium bicarbonate and saturated brine and dried over anhydrous sodium sulfate, the drying agent was removed by filtration, and then the resulting filtrate was concentrated under reduced pressure and purified by a flash column chromatography (silica gel: Wako Gel C200 (manufactured by Wako Pure Chemical Industries), eluant: hexane-ethyl acetate=20.1) to obtain 55.23 g of N-t-butoxycarbonyl-4-(4-fluorobenzylidene) piperidine. The thus obtained oily product was crystallized after its overnight standing at room temperature.

m.p. 69–70° C.

475 ml of 4 N hydrogen chloride in dioxane was added to 55.00 g of N-t-butoxycarbonyl-4-(4-fluorobenzylidene) piperidine in an ice bath, and the mixture was stirred at room temperature for 2 hours. The reaction solution was concentrated under reduced pressure, and the resulting crystals were recrystallized from isopropanol to obtain 40.72 g of 4-(4-fluoroobenzylidene)piperidine hydrochloride.

m.p. 184–185.5° C.

Structures and physical property data of this compound and other compounds obtained in the same manner are shown in Table 2.

In the case of the synthesis of α-alkylbenzylidenepiperidine derivatives, lithium diisopropylamide was used as the base in stead of sodium hydride (containing 15-crown-5 ether), and the reaction temperature was increased to room temperature after the dropwise addition at −50° C.

TABLE 1

$$R^1-\underset{\underset{O}{\|}}{C}-\underset{S}{\overset{N}{\diagup}}\diagdown\underset{(CH_2)_n-N}{Ar^1} \cdot HX \quad Y^1-Y^2-Ar^2$$

| Comp. No. | Ex. No. | $Ar^1$ | $R^1$ | n | $Y^1-Y^2$ | $Ar^2$ | HX | m.p. (° C.) Recrystallization Solvent |
|---|---|---|---|---|---|---|---|---|
| A-01 | 2 | 4-F-C6H4 | EtO | 2 | C=CH | 4-F-C6H4 | HCl | 202.0–203.0 (EtOH) |
| A-02 | 3 | 4-F-C6H4 | H$_2$N | 2 | C=CH | 4-F-C6H4 | — | 139.5–140.5 (EtOH)*[1] |

TABLE 1-continued

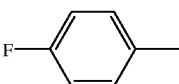

| Comp. No. | Ex. No. | Ar¹ | R¹ | n | Y¹—Y² | Ar² | HX | m.p. (° C.) Recrystallization Solvent |
|---|---|---|---|---|---|---|---|---|
| A-03 | 3 | 4-F-C₆H₄ | MeHN | 2 | C≡CH | 4-F-C₆H₄ | HCl | 204.0–206.0 (IPA)*¹ |
| A-04 | 3 | 4-F-C₆H₄ | Me₂N | 2 | C≡CH | 4-F-C₆H₄ | HCl | 229.0–233.0 (IPA)*¹ |
| A-05 | 3 | 4-F-C₆H₄ | pyrrolidinyl | 2 | C≡CH | 4-F-C₆H₄ | HCl | 224.0–227.0 (IPA)*¹ |
| A-06 | 3 | 4-F-C₆H₄ | morpholinyl | 2 | C≡CH | 4-F-C₆H₄ | — | 130.0–133.5 (IPE)*¹ |
| A-07 | 3 | 4-F-C₆H₄ | piperazinyl | 2 | C≡CH | 4-F-C₆H₄ | — | 103.0–105.0 (IPE)*¹ |
| A-08 | 3 | 4-F-C₆H₄ | 4-Me-piperazinyl | 2 | C≡CH | 4-F-C₆H₄ | — | 83.5–84.5 (IPE)*¹ |
| A-09 | 2 | 4-F-C₆H₄ | EtO | 2 | C≡CH | 3-F-C₆H₄ | HCl | 206.5–207.5 (EtOH) |
| A-10 | 3 | 4-F-C₆H₄ | H₂N | 2 | C≡CH | 3-F-C₆H₄ | — | 171.5–172.5 (EtOH)*¹ |
| A-11 | 4 | 4-F-C₆H₄ | KO | 2 | C≡CH | 3-F-C₆H₄ | — | Amorphous*³ |
| A-12 | 2 | 4-F-C₆H₄ | EtO | 2 | C≡CH | C₆H₅ | HCl | 178.0–181.0 (IPA) |
| A-13 | 3 | 4-F-C₆H₄ | H₂N | 2 | C≡CH | C₆H₅ | — | 150.0–151.0 (EtOH) |

TABLE 1-continued

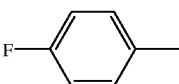

| Comp. No. | Ex. No. | Ar¹ | R¹ | n | Y¹—Y² | Ar² | HX | m.p. (° C.) Recrystallization Solvent |
|---|---|---|---|---|---|---|---|---|
| A-14 | 2 | F—C₆H₄— | EtO | 2 | C=CH | —C₆H₄—Me | HCl | 181.5–183.0 (EtOH) |
| A-15 | 3 | F—C₆H₄— | H₂N | 2 | C=CH | —C₆H₄—Me | HCl | 132.0–135.5 (IPA-IPE) |
| A-16 | 2 | C₆H₅— | EtO | 2 | C=CH | —C₆H₄—F | HCl | 192.5–194.0 (EtOH) |
| A-17 | 3 | C₆H₅— | H₂N | 2 | C=CH | —C₆H₄—F | HCl | 188.0(dec)*² (IPA-IPE) |
| A-18 | 3,5 | C₆H₅— | H₂N | 2 | C=CH | —C₆H₄—F | — | 157.0–158.0 AcOEt) |
| A-19 | 2 | Me—C₆H₄— | EtO | 2 | C=CH | —C₆H₄—F | HCl | 150.0–152.0 (IPA) |
| A-20 | 3 | Me—C₆H₄— | H₂N | 2 | C=CH | —C₆H₄—F | HCl | 165.0(dec)*² (IPA-IPE) |
| A-21 | 2 | F—C₆H₄— | EtO | 2 | CH—C(O) | —C₆H₄—F | HCl | 193.5(dec.)*² (EtOH) |
| A-22 | 3 | F—C₆H₄— | H₂N | 2 | CH—C(O) | —C₆H₄—F | — | 166.5–167.5 (EtOH)*¹ |
| A-23 | 4 | F—C₆H₄— | KO | 2 | CH—C(O) | —C₆H₄—F | — | Amorphous*⁴ |

Comp. No.: Compound number
Ex. No.: Example number used for synthesizing corresponding compound
Recrystallization solvent; EtOH; ethanol, IPA: isopropyl alcohol, IPE: diisopropyl ether
*¹Crystallization solvent
*²Decomposition temperature
*³Compound A-11
NMR (CDCl₃) δ (ppm); 2.30–2.63(10H, m), 3.00–3.10(2H, m), 6.30(1H, s), 6.99–7.07(3H, m), 7.23–7.43(3H, m), 7.62–7.69(2H, m)MS m/e; 517(M⁺+K), 479(M⁺+1), 204(100%)
*⁴Compound A-23
NMR (CDCl₃) δ (ppm); 1.54–1.82(4H, m), 2.22–2.32(2H, m), 2.62–2.69(2H, m), 2.98–3.10(4H, m), 3.35–3.45(1H, m), 7.22–7.42(4H, m), 7.59–7.68(2H, m), 8.02–8.11(2H, m) MS m/e; 533(M⁺+K), 495(M⁺+1), 154(100%)

TABLE 2

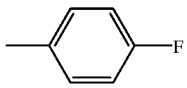

| Comp. No. | Ar² | R² | HX | m.p. (° C.) | Recrystal- lization Solvent |
|---|---|---|---|---|---|
| B-01 | 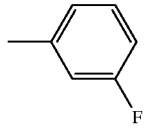 4-F-phenyl | H | HCl | 184.0–185.5 | IPA |
| B-02 | 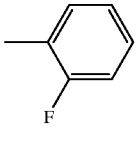 3-F-phenyl | H | HCl | 199.0–200.5 | IPA |
| B-03 | 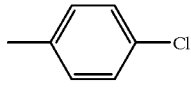 2-F-phenyl | H | HCl | 196.5–197.5 | IPA |
| B-04 | 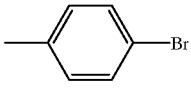 4-Cl-phenyl | H | HCl | 207.0–208.0 | IPA |
| B-05 | 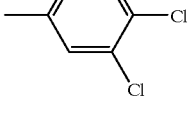 4-Br-phenyl | H | HCl | 207.0–208.5 | IPA |
| B-06 | 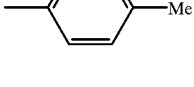 3,4-diCl-phenyl | H | HCl | 183.5–185.0 | IPA |
| B-07 | 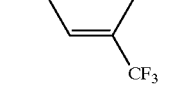 4-Me-phenyl | H | HCl | 223.0–224.0 | IPA |
| B-08 | 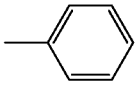 3-CF₃-phenyl | H | HCl | 138.0–139.0 | IPA-IPE |
| B-09 |  phenyl | H | HCl | 187.5–188.5 | IPA |
| B-10 | 4-OMe-phenyl | H | HCl | 178.5–179.5 | IPA |
| B-11 | 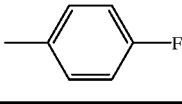 4-F-phenyl | Me | HCl | 137.0–138.0 | IPA-IPE |

Comp. No.: Compound number
Recrystallization solvent; IPA: isopropyl alcohol, IPE: diisopropyl ether Test Example (Receptor Binding Test)

1. Dopamine $D_4$ receptor binding test

Chinese hamster ovary (CHO) cell membrane, in which human $D_{4.2}$ receptor was expressed, was used as a receptor sample.

[$^3$H] Spiperone was used as a [$^3$H]-labeled ligand.

The binding reaction using the [$^3$H]-labeled ligand was carried out by the following method described in Eur. J. Pharmacol., 233, 173 (1993).

Human $D_{4.2}$ receptor binding test: The CHO cell membrane, in which human $D_{4.2}$ receptor has been expressed, [$^3$H] spiperone (0.5 nM) and each test compound were allowed to undergo 2 hours of reaction at 27° C. in 50 mM Tris-HCl buffer (pH 7.4) containing 5 mM EDTA, 1.5 mM CaCl$_2$, 5 mM KCl and 120 mM NaCl.

After completion of the reaction, the reaction solution was filtered by suction through a glass filter (GF/B), and radioactivity on the filter paper was measured using a liquid scintillation spectrometer.

The binding when the reaction was carried out in the presence of 10 μM haloperidol was defined as non-specific binding of [$^3$H] spiperone, and the difference between total binding and non-specific binding was defined as specific binding. An inhibition curve was obtained by allowing a fixed concentration of [$^3$H] spiperone to react with varied concentration of each compound to be tested under the aforementioned conditions, and the concentration of each test compound which inhibits 50% of the [$^3$H] spiperone binding (IC$_{50}$) was calculated from the inhibition curve, with the results shown in Table 3.

2. Dopamine $D_2$ receptor binding test

Rat striate body membrane was used as a receptor sample. [$^3$H] Raclopride was used as a [$^3$H]-labeled ligand.

The binding reaction using the [$^3$H]-labeled ligand was carried out by the following method described in Mol Pharmacol., 43, 749 (1993).

Preparation of receptor sample: Rat striate body was homogenized in 50 mM Tris-HCl buffer (pH 7.4) and centrifuged at 48,000×g, and the precipitate was washed once with water. The precipitate was suspended in 50 mM Tris-HCl buffer (pH 7.4) containing 120 mM NaCl, 5 mM KCl, 2 mM CaCl$_2$ and 1 mM MgCl$_2$, and used as a membrane sample.

Dopamine $D_2$ receptor binding test: The membrane sample (0.5 mg protein/ml), [$^3$H] raclopride (1 nM) and each test compound were allowed to undergo 1 hour of reaction at 25° C.

After completion of the reaction, the reaction solution was filtered by suction through a glass filter (GF/B), and radioactivity on the filter paper was measured using a liquid scintillation spectrometer.

The binding when the reaction was carried out in the presence of 10 μM haloperidol was defined as non-specific binding of [$^3$H] raclopride, and the difference between total binding and non-specific binding was defined as specific binding. An inhibition curve was obtained by allowing a fixed concentration of [$^3$H] raclopride to react with varied concentration of each compound to be tested under the aforementioned conditions, and the concentration of each test compound which inhibits 50% of the [$^3$H] raclopride binding (IC$_{50}$) was calculated from the inhibition curve, with the results shown in Table 3.

TABLE 3

| Comp. No.*[1] | IC$_{50}$ (nM) | |
|---|---|---|
| | D$_4$ | D$_2$ |
| A-02 | 5.46 | ≧1000 |
| A-09 | 13.9 | >1000 |
| A-10 | 4.53 | 559.1 |
| A-11 | 10.5 | ≧1000 |
| A-13 | 3.13 | 142.8 |
| A-15 | 18.3 | 432.9 |
| A-17 | 5.99 | 628.0 |
| A-20 | 9.55 | 187.4 |
| A-21 | 3.43 | >1000 |
| A-22 | 3.13 | 72.2 |

*[1]:Compound number (the same as Table 1)

INDUSTRIAL APPLICABILITY

The compound of the present invention has superior affinity for dopamine D$_4$ receptor but low affinity for dopamine D$_2$ receptor, thus showing excellent selectivity.

In consequence, the compound of the present invention is useful as a drug for the prevention and treatment of diseases such as schizophrenia and problematic behavior caused by cerebrovascular accidents and senile dementia and also as said drug which does not induce extrapyramidal disorders as side effects.

We claim:

1. A 2-carbonylthiazole compound represented by the formula:

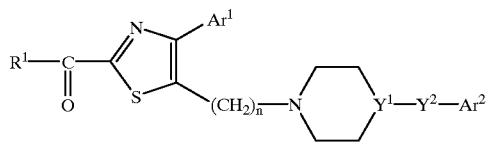

(I)

wherein each of Ar$^1$ and Ar$^2$ represents a phenyl group, a thienyl group, or a phenyl group having one or two substituents selected from a halogen atom, an alkyl group having 1 to 5 carbon atoms, a trifluoromethyl group, an alkoxy group having 1 to 5 carbon atoms and a hydroxyl group; R$^1$ represents an alkoxy group having 1 to 5 carbon atoms, a hydroxyl group or an amino group represented by formula NR$^3$R$^4$, wherein each of R$^3$ and R$^4$ represents a hydrogen atom or an alkyl group having 1 to 5 carbon atoms, or R$^3$ and R$^4$, together with the nitrogen atom to which they are bound, form a pyrrolidino, piperidino, morpholino or piperazino group, or a pyrrolidino, piperidino, morpholino or piperazino group having one to four substituents selected from an alkyl group having 1 to 5 carbon atoms, an alkoxy group having 1 to 5 carbon atoms and a hydroxyl group; Y$^1$–Y$^2$ represents CH—CO or C=CR$^2$, wherein R$^2$ represents a hydrogen atom or an alkyl group having 1 to 5 carbon atoms; and n is an integer of from 1 to 4 or a pharmaceutically acceptable salt thereof.

2. A 2-carbonylthiazole compound represented by the formula:

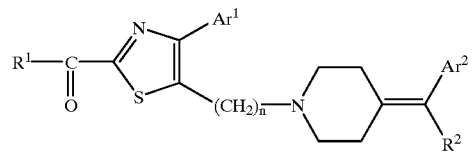

wherein each of Ar$^1$ and Ar$^2$ represents a phenyl group, a thienyl group, a phenyl group having one or two substituents selected from a halogen atom, an alkyl group having 1 to 5 carbon atoms, a trifluoromethyl group, an alkoxy group having 1 to 5 carbon atoms and a hydroxyl group; R$^1$ represents an alkoxy group having 1 to 5 carbon atoms, a hydroxyl group or an amino group represented by formula NR$^3$R$^4$;

wherein each of R$^3$ and R$^4$ represents a hydrogen atom or an alkyl group having 1 to 5 carbon atoms, or R$^3$ and R$^4$, together with the nitrogen atom to which they are bound, form a pyrrolidino, piperidino, morpholino or piperazino group, or a pyrrolidino, piperidino, morpholino or piperazino group having one to four substituents selected from an alkyl group having 1 to 5 carbon atoms, an alkoxy group having 1 to 5 carbon atoms and a hydroxyl group; R$^2$ represents a hydrogen atom or an alkyl group having 1 to 5 carbon atoms; and n is an integer of from 1 to 4 or a pharmaceutically acceptable salt thereof.

3. A 2-carbonylthiazole compound represented by formula:

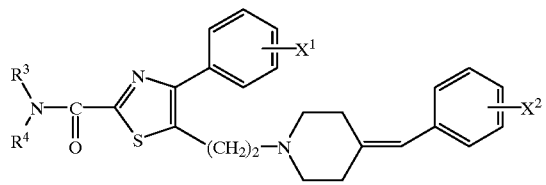

wherein each of X$^1$ and X$^2$ represents a hydrogen atom, a halogen atom or an alkyl group having 1 to 5 carbon atoms; and each of R$^3$ and R$^4$ represents a hydrogen atom or an alkyl group having 1 to 5 carbon atoms, or R$^3$ and R$^4$, together with the nitrogen atom to which they are bound, form a pyrrolidino, piperidino, morpholino or piperazino group or a pyrrolidino, piperidino, morpholino or piperazino group having one to four substituents selected from "an alkyl group having 1 to 5 carbon atoms, an alkoxy group having 1 to 5 carbon atoms and a hydroxyl group" or a pharmaceutically acceptable salt thereof.

4. The 2-carbonylthiazole compound or a pharmaceutically acceptable salt thereof according to claim 3, wherein R$^3$ and R$^4$ are hydrogen atoms.

5. The 2-carbonylthiazole compound or a pharmaceutically acceptable salt thereof according to claim 4, wherein X$^1$ and X$^2$ are both 4-position substituted fluorine atoms, X$^1$ is a hydrogen atom and X$^2$ is a 4-position substituted fluorine atom, or X$^1$ is a 4-position substituted fluorine atom and X$^2$ is a 3-position substituted fluorine atom.

6. A 2-carbonylthiazole compound represented by a formula:

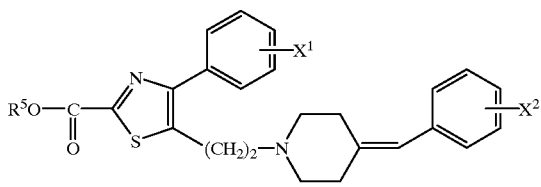

wherein each of $X^1$ and $X^2$ represents a hydrogen atom, a halogen atom or an alkyl group having 1 to 5 carbon atoms, and $R^5$ represents an alkyl group having 1 to 5 carbon atoms, or a pharmaceutically acceptable salt thereof.

7. A composition which comprises the 2-carbonylthiazole compound or a pharmaceutically acceptable salt thereof as defined in claim 1 and and at least one additive selected from the group consisting of fillers, binders, disintegrating agents, pH adjusting agents and solubilizing agents.

8. A dopamine D receptor antagonist composition comprising; the 2-carbonylthiazole compound or a pharmaceutically acceptable salt thereof as defined in claim 1 as its active ingredient and at least one additive selected from the group consisting of fillers, binders, disintegrating agents, pH adjusting agents and solubilizing agents.

* * * * *

UNITED STATES PATENT AND TRADEMARK OFFICE
CERTIFICATE OF CORRECTION

PATENT NO.    : 6,166,033
DATED         : December 26, 2000
INVENTOR(S)   : Nakazato et al.

It is certified that error appears in the above-identified patent and that said Letters Patent is hereby corrected as shown below:

Column 3,
Line 25, "$(CH_2)_n$" should read -- $(CH_2)_2$ --.

Column 10,
Line 67, "Chloride" should read -- chloride --.

Column 11,
Lines 15+, "$Ph_3P^1$" should read -- $Ph_3P^+$ --.

Column 14,
Line 65, "piperidine)." should read -- piperidine --.

Columns 15 and 16,
In the first formula of Table 1, "IIX" should read -- HX --; and Columns 15-16, 17-18, and 19-20,
In the first formula of Table 1, the double bond is missing from the 5-member ring.

Column 19,
Third line under the Table, "IPF" should read -- IPE --.

Column 21,
Line 10, "IIX" should read -- HX --.

Column 22,
Line 38, "$^3II$" should read -- $^3H$ --.

UNITED STATES PATENT AND TRADEMARK OFFICE
CERTIFICATE OF CORRECTION

PATENT NO. : 6,166,033
DATED : December 26, 2000
INVENTOR(S) : Nakazato et al.

It is certified that error appears in the above-identified patent and that said Letters Patent is hereby corrected as shown below:

<u>Column 24,</u>
Line 52, ""an" should read -- an --;
Line 54, "group""should read -- group --.

Signed and Sealed this

Twenty-sixth Day of February, 2002

Attest:

JAMES E. ROGAN
*Attesting Officer*     *Director of the United States Patent and Trademark Office*